US006785572B2

(12) United States Patent
Yanof et al.

(10) Patent No.: US 6,785,572 B2
(45) Date of Patent: Aug. 31, 2004

(54) TACTILE FEEDBACK AND DISPLAY IN A CT IMAGE GUIDED ROBOTIC SYSTEM FOR INTERVENTIONAL PROCEDURES

(75) Inventors: Jeffrey Harold Yanof, Solon, OH (US); Karl J. West, Geneva, OH (US); Christopher Bauer, Westlake, OH (US); David Morgan Kwartowitz, Elmont, NY (US)

(73) Assignee: Koninklijke Philips Electronics, N.V., Eindhoven (NL)

( * ) Notice: Subject to any disclaimer, the term of this patent is extended or adjusted under 35 U.S.C. 154(b) by 247 days.

(21) Appl. No.: 09/990,122

(22) Filed: Nov. 21, 2001

(65) Prior Publication Data

US 2003/0097060 A1 May 22, 2003

(51) Int. Cl.[7] .................................................. A61B 5/05
(52) U.S. Cl. ........................ 600/427; 600/411; 901/34; 901/8; 901/9; 901/14
(58) Field of Search .................................. 600/407, 568, 600/411, 427, 428, 424, 595; 434/262, 267; 345/702; 606/130; 318/568.21, 568.16; 901/1, 2, 14, 9, 30–36

(56) References Cited

U.S. PATENT DOCUMENTS

| | | | |
|---|---|---|---|
| 5,339,799 A | | 8/1994 | Kami et al. ...................... 128/4 |
| 5,343,391 A | * | 8/1994 | Mushabac ...................... 433/76 |
| 5,737,505 A | * | 4/1998 | Shaw et al. ................... 345/419 |
| 5,776,126 A | * | 7/1998 | Wilk et al. ...................... 606/1 |
| 5,984,880 A | * | 11/1999 | Lander et al. ............... 600/595 |
| 6,042,555 A | * | 3/2000 | Kramer et al. .............. 600/595 |
| 6,064,904 A | | 5/2000 | Yanof et al. |
| 6,106,301 A | | 8/2000 | Merril |
| 6,113,395 A | * | 9/2000 | Hon ............................ 434/262 |
| 6,184,868 B1 | * | 2/2001 | Shahoian et al. ............ 345/161 |
| 6,245,028 B1 | * | 6/2001 | Furst et al. .................. 600/568 |
| 6,468,226 B1 | * | 10/2002 | McIntyre, IV ............... 600/564 |
| 6,496,200 B1 | * | 12/2002 | Snibbe et al. ................ 345/701 |
| 6,642,686 B1 | * | 11/2003 | Ruch ....................... 318/568.21 |
| 6,665,554 B1 | * | 12/2003 | Charles et al. .............. 600/427 |
| 2002/0133174 A1 | * | 9/2002 | Charles et al. .............. 606/130 |
| 2003/0210259 A1 | * | 11/2003 | Liu et al. ..................... 345/702 |

FOREIGN PATENT DOCUMENTS

| | | |
|---|---|---|
| EP | 1 103 223 A2 | 5/2001 |
| EP | 1 103 229 A2 | 5/2001 |
| WO | WO 00/28882 | 5/2000 |
| WO | WO 01/76497 A1 | 10/2001 |

\* cited by examiner

Primary Examiner—Eleni Mantis Mercader
(74) Attorney, Agent, or Firm—Fay, Sharpe, Fagan, Minnich & McKee, LLP

(57) ABSTRACT

A system (10) for conducting an image-guided medical procedure on a subject (20) includes a medical imaging apparatus (100) which intermittently during the procedure obtains, upon demand, real-time medical images of the actual procedure. A robotic arm (200) hold a medical instrument (e.g., a biopsy needle (210)) that is used to perform the procedure. The robotic arm (200) manipulates the medical instrument in response to drive signals from a haptic control (400). A detector (e.g., a strain gauge (230)) measures forces experienced by the medical instrument during the procedure. The haptic control (400) generates the drive signals in response to manipulations of an input device (e.g., a knob (404) or an auxiliary instrument, such as, in the case of a biopsy, a remote needle (500)) by an operator, and the operator receives tactile feedback from the haptic control (400) in accordance with the measured forces experienced by the medical instrument. A display (e.g., a video monitor (152)) shows a virtual planning view of the procedure. The virtual planning view depicts a pre-procedure image (310) of the subject (20) with a virtual medical instrument (e.g., a virtual needle (300)) corresponding to the medical instrument held by the robotic arm (200) superimposed therein. In response to the drive signals from the haptic control (400), the virtual medical instrument has its position and orientation updated relative to the pre-procedure image (310).

20 Claims, 5 Drawing Sheets

TACTILE FEEDBACK AND DISPLAY IN A CT IMAGE GUIDED ROBOTIC SYSTEM FOR INTERVENTIONAL PROCEDURES

BACKGROUND OF THE INVENTION

The present invention relates to image guided interventional medical procedures. It finds particular application in conjunction with computed tomography (CT) imaging systems and robot assisted needle biopsies, and will be described with particular reference thereto. However, it is to be appreciated that the present invention is also amenable to other like applications using different imaging modalities and/or for different medical procedures.

It is often desired that interventional medical procedures be as minimally invasive as possible. However, it is also desirable to be able to visualize or otherwise know the relative positions and/or orientations of surgical tools or devices with respect to surrounding anatomy. The latter goal may be achieved by a direct inspection of the anatomy. However, in the case of interior anatomy, direct inspection may be more invasive than desired insomuch as additional or larger incisions may have to be made to expose or access the interior anatomy for direct inspection.

For example, it is often desirable to sample or test a portion of tissue from human or animal subjects, particularly in the diagnosis and treatment of potentially cancerous tumors, pre-malignant conditions, and other diseases or disorders. Typically, in the case of tumors, when the physician suspects that cancer or an otherwise diseased condition exists, a biopsy is performed to determine if in fact cells from the tumor are cancerous or otherwise diseased. Many biopsies, such as percutaneous biopsies, are performed with a needle-like instrument used to collect the cells for analysis.

In recent years, the performance of interventional medical procedures such as needle biopsies has been enhanced by the use of x-ray imaging, CT scans, continuous CT (CCT), magnetic resonance imaging (MRI), fluoroscopy, single photon emission CT (SPECT), positron emission tomography (PET), and the like. The imaging equipment allows an interventionalist, such as a radiologist, surgeon, physician, or other medical personnel, to track the insertion of interventional devices, such as biopsy needles, in a subject during diagnostic and therapeutic procedures. While such imaging modalities allow procedures to be performed with minimal invasiveness and are helpful to the interventionalist and the patient, they have certain drawbacks.

For example, with some image-guided procedures, e.g., those using CT imaging, the tracking of the needle position is not done in real-time. That is to say, a static image is obtained and the needle position noted therein. Subsequently, the needle is advanced or retracted by a small amount and another static image obtained to verify the new needle position. This sequence is repeated as many times as necessary to track the needle's progression. Such a procedure tends to be time consuming insomuch as the needle progresses by only a short distance or increment between imaging, and needle progression is halted during imaging. Moreover, accuracy suffers to the extent that in the interim, i.e., between images, the needle's position cannot be visualized.

With the development of CCT imaging and fluoroscopy, real-time imaging has been made possible. In CCT scanning, a rotating x-ray source irradiates the subject continuously, generating images at a rate of approximately six frames per second. The use of CCT or fluoroscopy by the interventionalist for real-time guidance and/or tracking of the needle during biopsies is gaining popularity. As a result, biopsies have become not only more accurate, but also shorter in duration. However, because of the imaging proceeds continuously, the patient and potentially the interventionalist are both exposed to a greater dose of radiation as compared to, e.g., non-continuous CT.

Accordingly, there exists in the prior art a trade-off between the level of radiation exposure experienced and real-time visualization of the procedure. That is to say, lower radiation exposure is conventionally achieved at the cost of real-time visualization, and conversely, real-time visualization is conventionally achieved at the cost of higher radiation exposure.

One problem resides in protecting the interventionalist from radiation exposure. In needle biopsies, for example, often the biopsy needle and guide are held within or close to the plane of the x-ray radiation so that the needle-tip will reside in the image plane thereby permitting continuous tracking. Staying close to the plane of imaging also, more often than not, allows for the distance the needle passes through the subject to be minimized. Consequently, this typically results in the interventionalist placing his/her hands in the x-ray beam. The hands of an interventionalist who performs several such procedures per day can easily receive a toxic dose of radiation. Therefore, it is desirable to provide interventionalists with a way to perform needle biopsies without the risk of radiation exposure.

A proposed approach to solving the aforementioned problem involves the use of a mechanical system which allows the interventionalist to manipulate the biopsy needle while his hands remain clear of the x-ray beam. However, such systems with mechanical linkages reduce or eliminate the tactile sensations (e.g., force, shear, and/or moment on the needle) otherwise available to an interventionalist directly manipulating the needle. This is disadvantageous in that interventionalists typically obtain useful information regarding the procedure from these tactile sensations. For example, they are often able to feel the needle transition between different tissue types, contact with bones, skin punch through, etc. The interventionalist generally desire this "feel" as they perform biopsies. To trained personnel, it serves as an additional indication of the needle's location.

Commonly owned U.S. Pat. No. 6,245,028 to Furst, et al., incorporated by reference herein in its entirety, addresses the lack of feel and interventionalist radiation exposure issues in part. However, insomuch as it employs a continuous imaging modality (e.g., CCT) radiation exposure to the patient may be higher than desirable.

The present invention contemplates a new and improved tactile feedback and display in an image guided robotic system for interventional procedures which overcomes the above-referenced problems and others.

BRIEF SUMMARY OF THE INVENTION

In accordance with one aspect of the present invention, a system for conducting an image-guided medical procedure on a subject is provided. The system includes a medical imaging apparatus which intermittently during the procedure obtains, upon demand, real-time medical images of the actual procedure. A robotic arm holds a medical instrument that is used to perform the procedure. The robotic arm manipulates the medical instrument in response to drive signals from a haptic control. A detector measures forces experienced by the medical instrument during the procedure. The haptic control generates the drive signals in response to manipulations of an input device by an operator, and the operator receives tactile feedback from the haptic control in accordance with the measured forces experienced by the medical instrument. A display shows a virtual planning view of the procedure. The virtual planning view depicts a pre-procedure image of the subject with a virtual medical instrument corresponding to the medical instrument held by the robotic arm superimposed therein. In response to the drive signals from the haptic control, the virtual medical instrument has its position and orientation updated relative to the pre-procedure image.

In accordance with another aspect of the present invention, a method of conducting a medical procedure on a subject includes planning the medical procedure by obtaining a pre-procedure image of the subject and superimposing therein a virtual medical instrument that corresponds to an actual medical instrument used to conduct the medical procedure. A robotic arm holding the actual medical instrument is remotely controlled to conduct the medical procedure, and forces experienced by the actual needle are measured as the medical procedure is being conducted. The method also includes providing tactile feedback to an operator conducting the procedure based on the measured forces, and updating a position and orientation of the virtual medical instrument in the pre-procedure image in accordance with the controlling of the robotic arm. Additionally, real-time images of the actual medical procedure are obtained intermittently during the medical procedure.

In accordance with another aspect of the present invention, an apparatus is provided for performing a medical procedure on a subject with a medical instrument. The apparatus includes: imaging means for intermittently during the procedure obtaining, upon demand, real-time medical images of the actual procedure; robotic means for holding the medical instrument used to perform the procedure, the robotic means manipulating the medical instrument in response to a first signal; force detecting means for measuring forces experienced by the medical instrument during the procedure; control means for generating the first signal in response to manipulations of an input device by an operator and for providing the operator tactile feedback in accordance with the measured forces experienced by the medical instrument; and, display means for showing a virtual planning view of the procedure, the virtual planning view depicting a pre-procedure image of the subject with a virtual medical instrument corresponding to the medical instrument held by the robotic means superimposed therein, the virtual medical instrument, in response to the first signal from the control means, having its position and orientation updated relative to the pre-procedure image.

One advantage of the present invention is that it guards against excessive radiation expose to both the interventionalist and the patient.

Another advantage of the present invention is that it provides tactile feedback to the operator.

Yet another advantage of the present invention is that it permits the interventionalist to continually monitor and/or visualize the progression of the procedure via a virtual view of the same while intermittently obtaining real-time images of the actual procedure for verification.

Still further advantages and benefits of the present invention will become apparent to those of ordinary skill in the art upon reading and understanding the following detailed description of the preferred embodiments.

BRIEF DESCRIPTION OF THE DRAWING(S)

The invention may take form in various components and arrangements of components, and in various steps and arrangements of steps. The drawings are only for purposes of illustrating preferred embodiments and are not to be construed as limiting the invention.

DETAILED DESCRIPTION OF THE PREFERRED EMBODIMENT(S)

Figure 1:
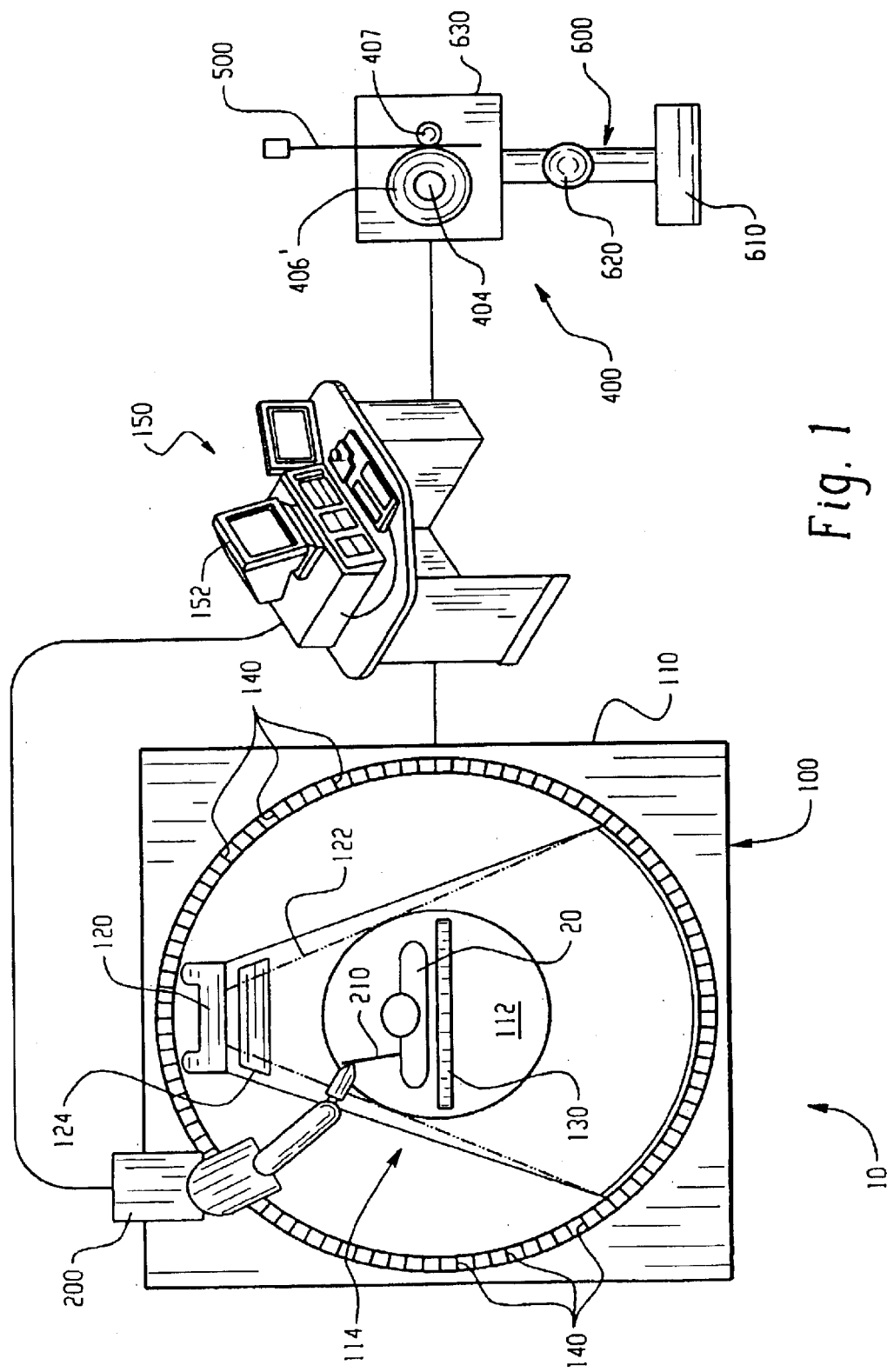
FIG. 1 is diagrammatic illustration of an exemplary image-guided interventional medical procedure system in accordance with aspects of the present invention which shows a front view of a haptic control included therein.

With reference to FIG. 1, an image-guided interventional medical procedure system 10 includes a diagnostic imaging apparatus 100 capable of generating medical diagnostic images of a subject 20. Optionally, the imaging apparatus 100 is an x-ray imaging device, CT scanner, CCT scanner, MRI scanner, fluoroscope, SPECT scanner, PET scanner, a combination or the foregoing or the like.

In the illustrated embodiment, the diagnostic imaging apparatus 100 is a CT scanner having a stationary gantry 110 which defines a central examination region 112. A rotating gantry 114 is mounted on the stationary gantry 110 for rotation about the examination region 112. A source of penetrating radiation 120, such as an x-ray tube, is arranged on the rotating gantry 114 for rotation therewith. The source of penetrating radiation produces a beam of radiation 122 that passes through the examination region 112 as the rotating gantry 114 rotates. A collimator and shutter assembly 124 forms the beam of radiation 122 into a thin fan-shape and selectively gates the beam 122 on and off. Alternately, the radiation beam 122 is gated on and off electronically at the source 120. Using an appropriate reconstruction algorithm in conjunction with the data acquired from the CT scanner, images of the subject 20 therein are selectively reconstructed.

A subject support 130, such as an operating table, couch or the like, suspends or otherwise holds the subject 20 received thereon, such as a human or animal patient, at least partially within the examination region 112 such that the thin fan-shaped beam of radiation 122 cuts a cross-sectional slice through the region of interest of the subject 20.

In the illustrated fourth generation CT scanner, a ring of radiation detectors 140 is mounted peripherally around the examination region 112 on the stationary gantry 110. Alternately, a third generation CT scanner is employed with an arc of radiation detectors 140 mounted on the rotating gantry 114 on a side of the examination region 112 opposite the source 120 such that they span the arc defined by the thin fan-shaped beam of radiation 122. Regardless of the configuration, the radiation detectors 140 are arranged to receive the radiation emitted from the source 120 after it has traversed the examination region 112.

In a source fan geometry, an arc of detectors which span the radiation emanating from the source 120 are sampled concurrently at short time intervals as the source 120 rotates behind the examination region 112 to generate a source fan view. In a detector fan geometry, each detector is sampled a multiplicity of times as the source 120 rotates behind the examination region 112 to generate a detector fan view. The paths between the source 120 and each of the radiation detectors 140 are denoted as rays.

The radiation detectors 140 convert the detected radiation into electronic projection data. That is to say, each of the radiation detectors 140 produces an output signal which is proportional to an intensity of received radiation. Optionally, a reference detector may detect radiation which has not traversed the examination region 112. A difference between the magnitude of radiation received by the reference detector and each radiation detector 140 provides an indication of the amount of radiation attenuation along a corresponding ray of a sampled fan of radiation. In either case, each radiation detector 140 generates data elements which correspond to projections along each ray within the view. Each element of data in the data line is related to a line integral taken along its corresponding ray passing through the subject being reconstructed.

With each scan by the CT scanner, the image data from the radiation detectors 140 is collected and reconstructed into an image representation of the subject 20 in the usual manner. For example, a data processing unit incorporated in a workstation and/or control console 150 collects the image data and reconstructs the image representation therefrom using rebinning techniques, convolution/backprojection algorithms, and/or other appropriate reconstruction techniques. In a preferred embodiment, the image representation, corresponding to the cross-sectional slice traversed by the thin fan-shaped beam of radiation 122 through the region of interest of the subject 20, is displayed on a human viewable display, such as a video monitor 152 or the like, which is also part of the console 160. The control console 150 is optionally remotely located with respect to the imaging apparatus 100 (e.g., in a shielded room adjacent the scanning room containing the imaging apparatus 100) and typically it includes one or more monitors 152, a computer or data processing hardware and/or software, one or more memories or other data storage devices, and one or more standard input devices (e.g., keyboard, mouse, trackball, etc.).

Figure 2:
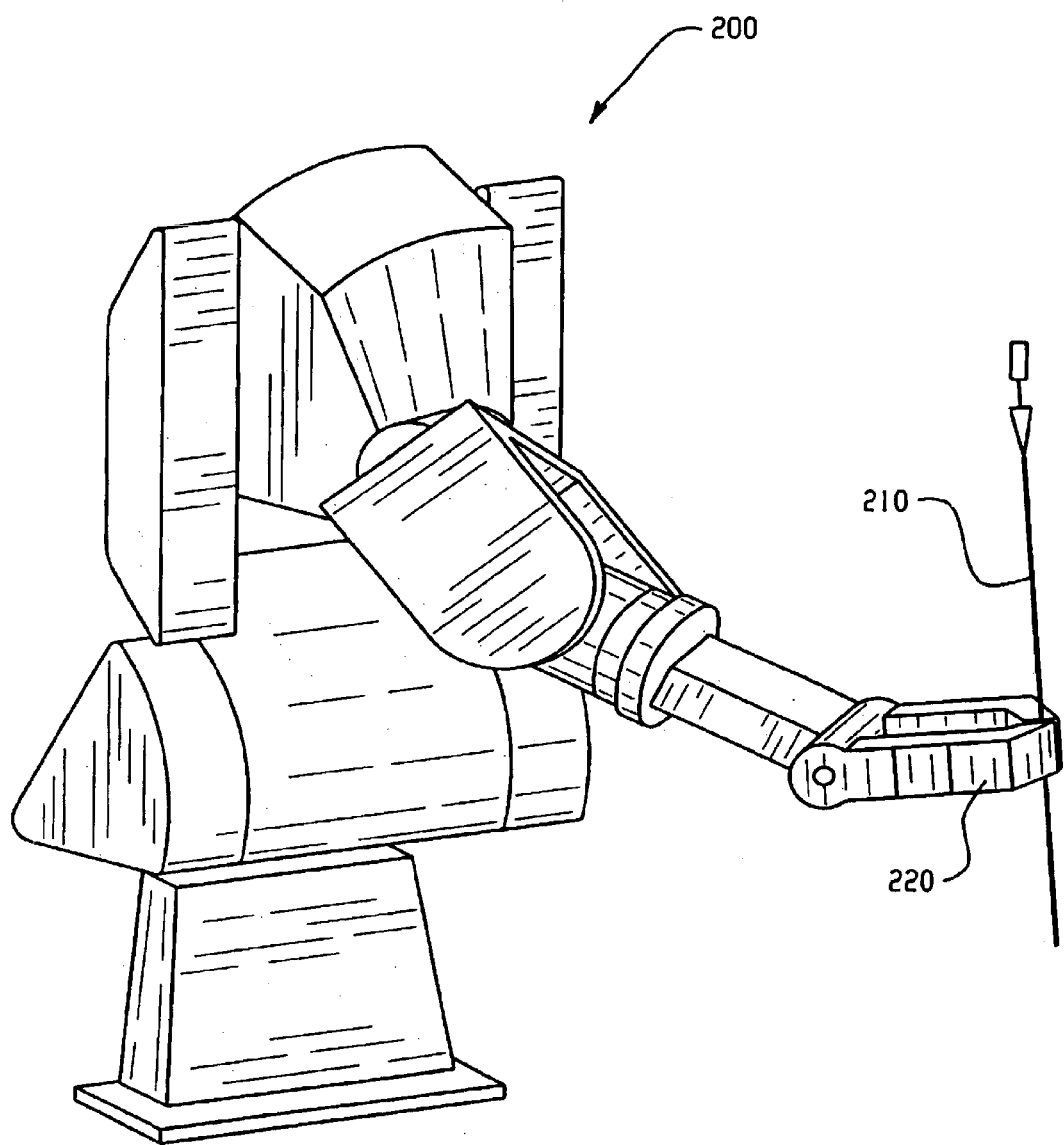
FIG. 2 shows a robotic arm holding a biopsy needle in accordance with aspects of the present invention.
Figure 3:
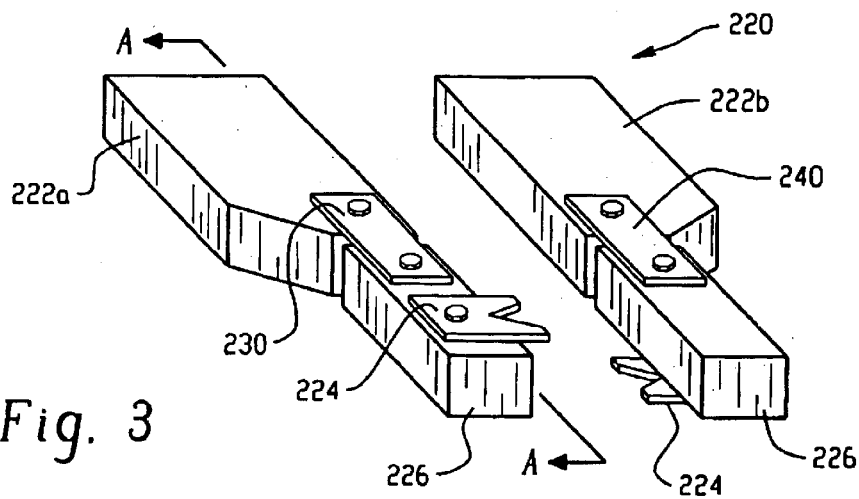
FIG. 3 is a perspective view showing a gripper of the robotic arm shown in FIG. 2.

With reference to FIG. 2 and continuing reference to FIG. 1, in a preferred embodiment, the image-guided interventional medical procedure system 10 also includes a robotic arm 200 which holds an interventional surgical tool or other like medical device, e.g., a biopsy needle 210, at a desire location and trajectory. The robotic arm 200 is preferably a fully adjustable multi-jointed multi-segmented arm with each joint having varying degrees of freedom. As will be described in greater detail later herein, the biopsy needle 210 is held by the robotic arm's gripper 220 (as best seen in FIG. 3). Accordingly, by appropriately arranging the robotic arm 200 (i.e., flexing or otherwise adjusting the multiple joints and/or segments) and by appropriately positioning the subject 20 and robotic arm 200 relative to one another, any arbitrary position and/or orientation of the biopsy needle 210 relative to the subject 20 is achieved as desired.

With reference to FIG. 3, the gripper 220 includes opposing portions 222a and 222b which can be selectively advanced toward and away from one another with a pneumatic or other similar drive to selectively hold and release, respectively, the biopsy needle 210 or other instrument positioned between instrument holding members 224 of an end-effector 226. The end-effector 226 is mechanically joined to the rest of the gripper 220 via a strain gauge 230 and a plurality of resilient spring members 240. Optionally, a load cell, pressure sensor or other like force measuring device may be used in lieu of the strain gauge 230 shown. Additionally, one or more of the spring members 240 may be replaced with an additional strain gauge 230.

The strain gauge 230 measures a force or forces experienced by the instrument held in the end-effector 226 and generates a force signal responsive or proportional thereto. For example, when an axial or other force is experienced by the biopsy needle 210 that force is transferred via the end-effector 226 to the strain gauge 230. The resulting deflection or force experienced by the strain gauge 230 causes the strain gauge 230 to produce a signal or voltage responsive or proportional thereto. When multiple strain gauges 230 are employed, their output signal is optionally averaged or otherwise similarly combined.

Figure 3A:
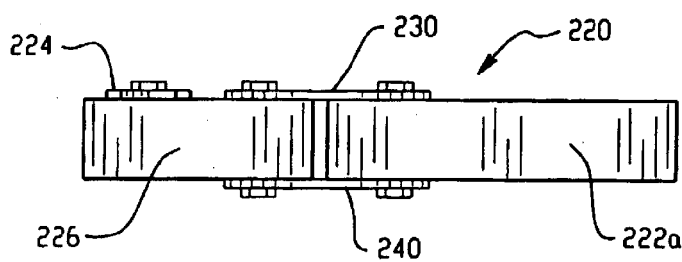
FIG. 3A is a cross-sectional side view of the gripper of FIG. 3 taken along section line A.

Preferably, four members (one strain gauge 230 and three resilient spring members 240) join the end-effector 226 to the rest of the gripper 220. As best seen in FIG. 3A, two juxtaposed members (one on top and one on bottom) join their respective portions of the end-effector 226 to opposing portions 222a and 222b, respectively. The juxtaposed members maintain or ensure substantially linear deflections of the end-effector 226 when a force or forces are experienced thereby. That is to say, they guard against unwanted canting or tilting of the end-effector 226, and hence, against unwanted canting or tilting of the biopsy needle 210 or other instrument held therein. The spring members 240 may also provide a damping mechanism to minimize the effect of vibrations at the end-effector 226 that may otherwise be undesirably transmitted via the strain gauge 230.

In accordance with a preferred embodiment, a diagnostic medical image or images of the region of interest of the subject 20 are obtained prior to conducting the interventional medical procedure. For example, where the procedure of interest is a biopsy, the pre-procedural or pre-operative images would be those axial slices or views which contain or are near the tumor or diseased anatomy. Optionally, the pre-operative images or image data is obtained with the imaging apparatus 100, or another diagnostic medical imaging device. Using the pre-operative image data, the interventionalist or other medical personnel plan the procedure via a virtual procedure planning system and/or method. An example of virtual procedure planning is found in commonly owned U.S. Pat. No. 6,064,904 to Yanof, et al., incorporated herein by reference in its entirety.

Figure 4:
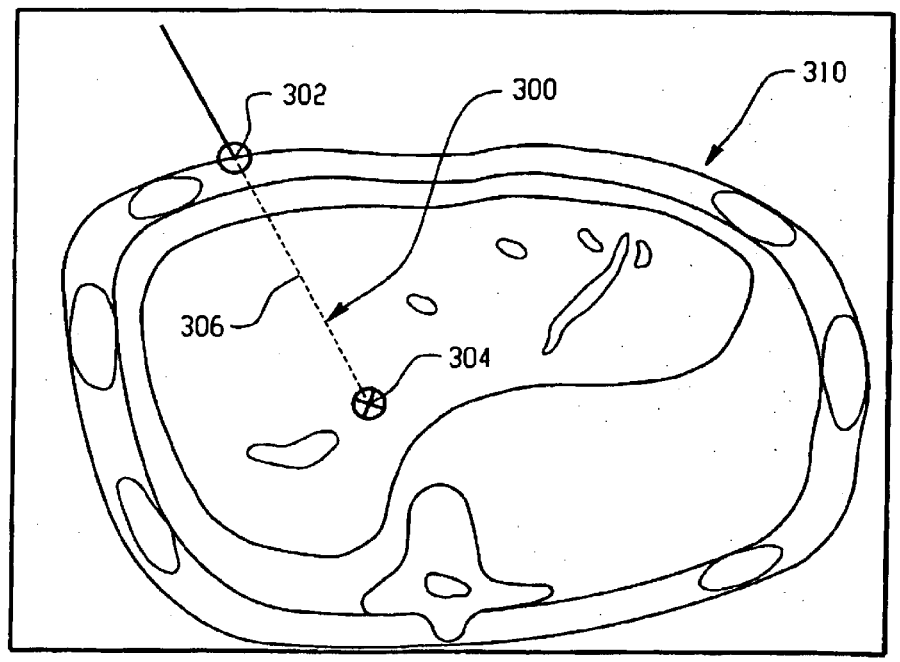
FIG. 4 is a virtual planning view in accordance with aspects of the present invention for an exemplary interventional medical procedure.

With reference to FIG. 4, the virtual procedure planning results in an image or images of the region of interest including superimposed therein a virtual surgical instrument, e.g., a virtual biopsy needle 300, which is at the desired orientation and position relative to the pre-operative images obtained. That is to say, the pre-operative images visualize the anatomy of interest 310, and via the virtual planning, a virtual needle 300 or other medical instrument is superimposed or otherwise incorporated therein at the desired position and trajectory for carrying out the procedure. In the illustrated embodiment, the virtual needle 300 is defined by an entry or percutaneous insertion point 302, a target point 304 and/or depth-to-target reading, and a needle trajectory 306 connecting the two points and/or an angulation reading. Collectively, the pre-operative or pre-procedural images with the virtual surgical or medical instrument depicted therein are referred to herein as the virtual and/or planning view. In a preferred embodiment, the virtual planning view includes the virtual needle 300 superimposed on a transverse axial slices or oblique plane containing the needle's trajectory. Using multi-planar reformatted (MPR) views, the needle's trajectory 306 is tracked in the virtual planning view regardless of whether or not it is in the transverse axial plane. That is to say, the virtual planning view is optionally generated from volumetric data and it can therefore show the complete trajectory of the virtual needle 300 for any arbitrary orientation, unlike the actual images generated by the CT scanner which can for the most part only readily obtain images of the transverse axial view. Accordingly, where the needle trajectory is not co-planar with the transverse axial view, visualization of the complete needle trajectory is not lost.

The virtual planning view is preferably loaded and/or maintained on the workstation or control console 150, or alternately, it is maintained on a separate computer, workstation or console from which it may be displayed and/or viewed by the interventionalist.

Figure 5:
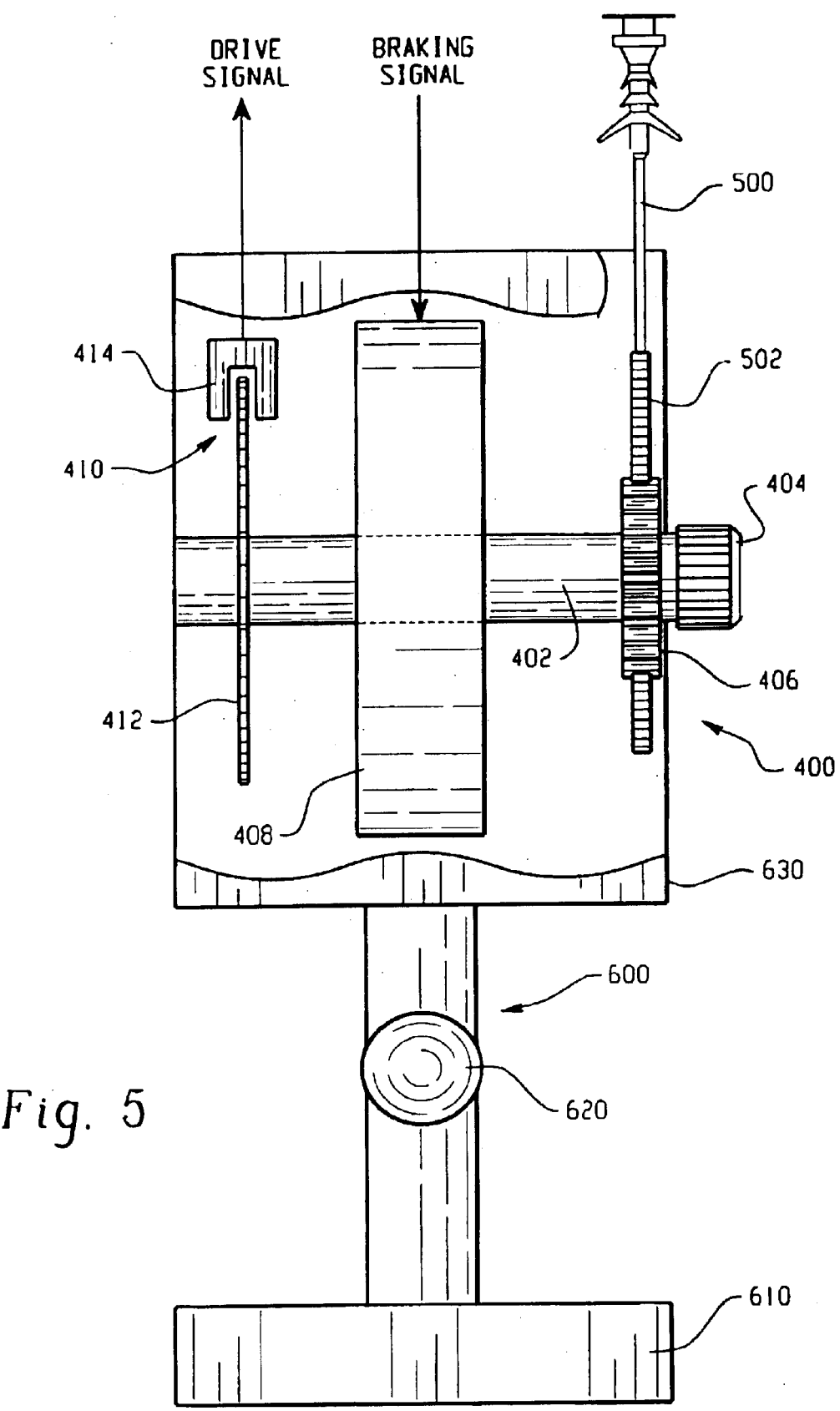
FIG. 5 shows a side view of a haptic control in accordance with aspects of the present invention.

With reference to FIG. 5, the system 10 also includes a haptic control 400 which is incorporated or in operative communication with the control console 150. The exemplary haptic control 400 illustrated includes: a common rotary shaft or axis 402 which has arranged thereon or otherwise interfaced therewith a knob 404, a pinion 406, a brake 408 and an optical encoder 410; an optional auxiliary or remote surgical or medical tool or instrument, such as a remote biopsy needle 500; and, an adjustable mount 600. The knob 404 allows for the direct rotation of the shaft 402 by an interventionalist or other operator of the haptic control 400. The pinion 406 mates with a rack 502 formed on, attached to or otherwise incorporated with the auxiliary or remote surgical or medical tool or instrument, such as the remote biopsy needle 500. The rack and pinion assembly effectuates the translation of linear movement of the auxiliary tool (i.e., the remote biopsy needle 500) to rotation of the shaft 402. Optionally, alternate assemblies may be used to achieve this translation of motion. For example, in one preferred embodiment (as best seen in FIG. 1), the pinion 406 is replaced with a wheel 406' having an essentially smooth (i.e., not cogged) perimeter surface optionally sheathed or otherwise covered with rubber or a similarly gripping material. The length of the remote needle 500 (absent the rack) or an otherwise linear member of the auxiliary tool is then press fit between the periphery of the wheel and an adjustable cam 407. In this manner, when the needle or linear member is advanced, its contact with the rubber or otherwise gripping periphery of the wheel effectuates the wheel's rotation, and hence, the rotation of the shaft 402. Additionally, alternate user controls other than the knob 404 or auxiliary tool may be employed, e.g., the user control may be an analog slider or the like.

The brake 408, in response to a braking signal, applies a variable frictional or other resistive force to the shaft 402 thereby regulating the ease or difficulty with which the shaft 402 is rotated. Optionally, e.g., the resistive force may be electro-magnetic or pneumatic in nature. In a preferred embodiment, the brake 408 is response to a voltage applied thereto and is of the "power-off" type. That is, when no voltage is applied to the brake 408, the brake 408 is fully engaged thereby essentially fixing the shaft 402 against rotation; and as voltage is progressively applied to the brake 406, the brake 408 progressively disengages to lessen the amount of torque which will rotate the shaft 402. Optionally, a power-on type brake may be employed.

The optical encoder 410 produces a drive signal responsive to the degree or amount of rotation of the shaft 402. In a preferred embodiment, the optical encoder 410 is a known type, e.g., including a radially etched or perforated disk 412 which rotates with the shaft 402, and an optical reader 414 that has a light emitting element (e.g., a photodiode or the like) and a light sensitive element (e.g., a photo-electric transducer or the like) on opposite sides of the disk 412. Accordingly, as the shaft 402 and disk 412 rotate, the light passing from the light emitting element to the light sensitive element is modulated in accordance with the perforations in the disk 412. In this manner, the optical encoder 410 measures the amount or degree of rotation of the shaft 402, and produces a drive signal responsive or proportional thereto. Optionally, other known devices for measuring the rotation movement of the shaft 402 may be employed.

The adjustable mount 600 includes a base 610 and a ball joint 620 (or other universal joint) through which the main body 630 of the haptic control 400 is mechanically joined to the base 610. The base 610 is used to secure the haptic control 400 to a tabletop or other work-surface. The joint 620 permits the main body 630 to be position or oriented as desired by the interventionalist or other operator of the haptic control 400 regardless of the orientation of the surface to which the base 610 is secured. Accordingly, e.g., the main body 630 may be oriented (regardless of the surface to which the haptic control 400 is secured) such that the trajectory of the remote biopsy needle 500 emulates that of the actual biopsy needle 210 thereby giving the interventionalist a more realistic feel to or perception of the procedure. That is to say, the orientation of the remote biopsy needle 500 may be made to correlate with the orientation of the actual biopsy needle 210.

Figure 6:
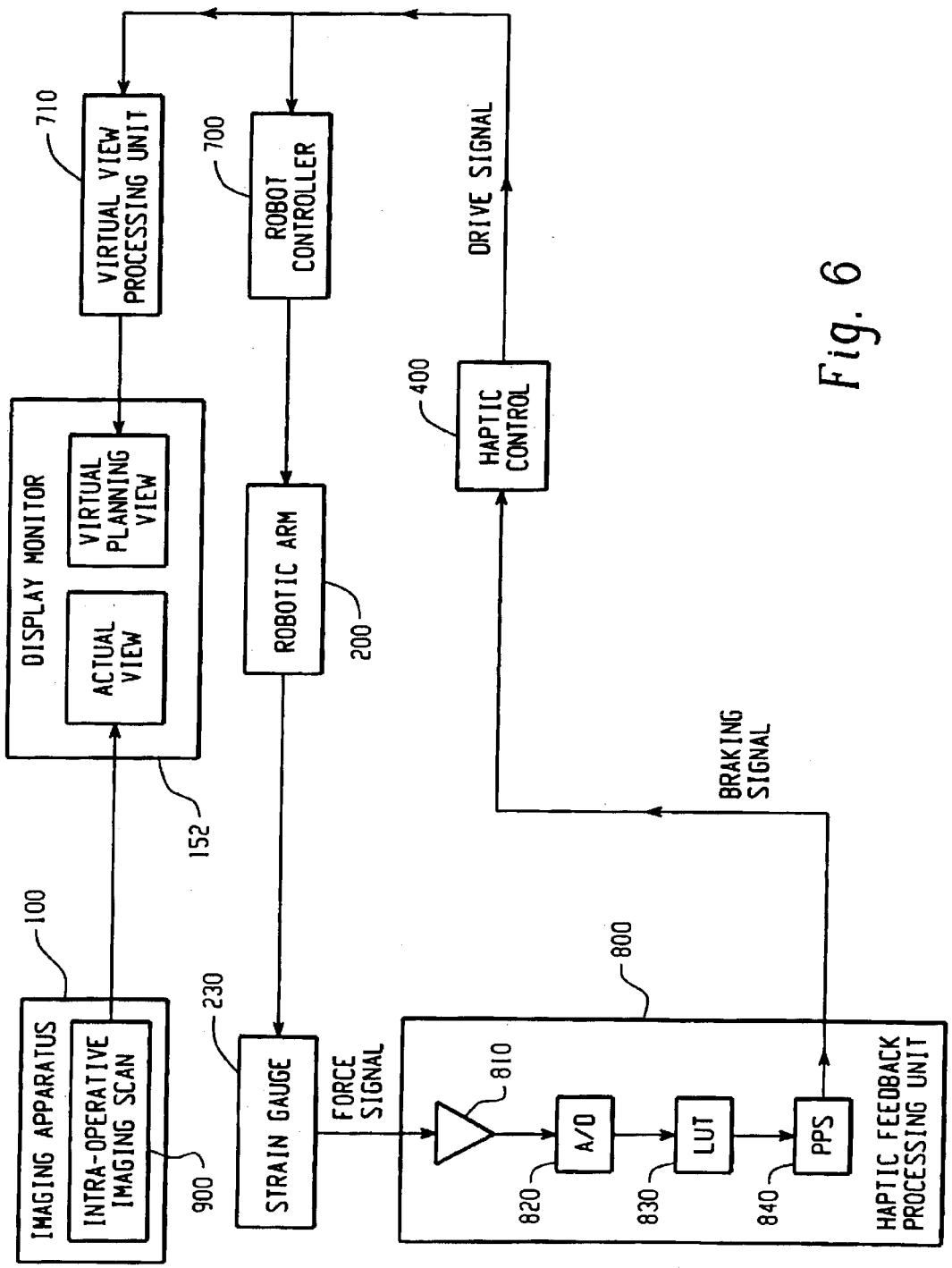
FIG. 6 is a block diagram showing the operation of an exemplary image-guided interventional medical procedure system in accordance with aspects of the present invention.

With reference to FIG. 6 and continuing reference to the preceding figures, an exemplary intra-operative procedure employing the system 10 will now be described. For purposes of this example, the procedure is a biopsy. Having appropriately positioned the subject or patient 20 within the examination region 112 of the imaging apparatus 100, the robotic arm 200 holding the biopsy needle 210 in the end-effector 226 of its gripper 220 is initially positioned and/or arranged such that the needle 210 corresponds to the virtual needle 300 in the virtual planning view, i.e., such that the actual needle's tip registers with the entry point 302 and the actual needle's orientation matches the planned trajectory 306. Optionally, the robotic arm 220 automatically moves to its initial positioning and/or arrangement based upon the virtual planning view maintain in the control console 150. That is to say, the interventionalist or other operator sends (from the control console or otherwise) the virtual planning view or data to a robot controller 700 which controls the movement of the robotic arm 200 accordingly. The robot controller 700 is optionally a dedicated processor or processing unit, incorporated in the control console 150, or otherwise.

The interventionalist then uses the haptic control 400 to drive the actual needle 210, i.e., selectively advance and/or retract the needle 210 along its trajectory. That is to say, by manipulating the knob 404 or the remote needle 500, the interventionalist imparts a desired amount or degree of rotation to the shaft 402. This rotation is measure by the optical encoder 410 which generates the drive signal responsive or proportional thereto. The drive signal is then communicated to the robot controller 700 which in response thereto directs the robotic arm 200 to drive the actual needle 210 accordingly along its trajectory. Preferably, there is a one-to-one correspondence between the amount of advancement and/or retraction of the remote needle 500 and the actual needle 210. For the knob 404, the amount of advancement and/or retraction of the actual needle 210 may be relatively scaled as desired. Optionally, the relative scaling can also be applied when the remote needle 500 is used, if desired.

In addition to communicating the drive signal to the robot controller 700, the drive signal is also communicated to a virtual view processing unit 710. The virtual view processing unit 710 updates the position of the virtual needle 300 in the virtual planning view display on the monitor 152 by advancing and/or retracting the virtual needle 300 along the planned trajectory 306 in accordance with the amount indicated by the drive signal. Preferably, the virtual processing unit 710 continually updates the virtual planning view in this manner as the drive signal varies due to manipulations of the haptic control 400. As with the robot controller 700, the virtual processing unit 710 is optionally a dedicated processor or processing unit, incorporated in the control console 150, or otherwise. Optionally, the advancement and/or retraction of the virtual needle 300 is indicated in the virtual view by: adjusting the depth-to-target reading; selectively switching portions of a line between a dashed, dotted or otherwise broken line which represents the remaining trajectory 306 not occupied by the needle, and a solid line representing the virtual needle 300; both of the foregoing; or otherwise as appropriate. In this manner, the interventionalist can visualize the progression of the procedure without having to continually image the patient 20, and hence, expose the patient 20 continually to the radiation beam 122.

In addition to monitoring the progress of the procedure via the virtual view, the interventionalist may intermittently, as desired or upon demand, conduct an intra-operative imaging experiment 900 with the imaging apparatus 100 to obtain a real-time image which visualizes the actual procedure. Herein, these intra-operative images are referred to as the actual view. Insomuch as the imaging is intermittent, the radiation exposure to the patient 20 is less than the exposure that would otherwise be experienced if the patient 20 were being continually imaged. Preferably, the actual view is displayed on the monitor 152 alongside the virtual view. Accordingly, the interventionalist may consult the periodically updated actual view and reference it against the continually updated virtual view to ensure that the actual procedure is in fact progressing as indicated in the virtual view.

As the actual needle 210 progresses or is moved by the robotic arm 200, it experiences forces. For example, axial forces are experienced as the needle 210 advances and/or retracts through tissue. Via the end-effector 226 holding the needle 210, these forces are in turn transferred to and/or deflect the strain gauge 230 which detects and/or measures the same and generates the force signal responsive or proportional thereto. The force signal is then fed through a haptic feedback processing unit 800 which conditions the force signal or otherwise generates the braking signal in response thereto. The braking signal is then applied to the brake 408 to thereby regulate the ease or difficulty with which the shaft 402 is rotated. In this manner, the interventionalist manipulating the haptic control 400 experiences tactile feedback representative of the forces experienced by the actual needle 210. That is to say, the haptic control 400 presents the interventionalist with essentially the same resistance or tactile feel he would experience if he were directly manipulating the actual needle 210. Optionally, if desired, the resistance or tactile feel presented by the haptic control 400 may be a scaled version of that which would be experience by the direct manipulation of the actual needle 210. The response time for the brake 408 to react to a force detected and/or measured by the strain gauge 230 is, preferably, less than approximately 100 msec, and more preferably, less than approximately 50 msec. Again, the feedback processing unit 800 or any component thereof is optionally a dedicated processor or processing unit, incorporated in the control console 150, or otherwise.

In a preferred embodiment, the feedback processing unit 800 includes an amplifier 810, an analog-to-digital (A/D) converter 820, a look-up table (LUT) 830, and a programmable power supply (PPS) 840. In operation, the force signal from the strain gauge 230 is amplified by the amplifier 810; the amplified signal (optionally, after low-pass filtering to remove noise) is then converted to a digital signal by the A/D converter 820; the digital signal is then used to access the LUT 830 which maps the force signal to a PPS control signal; and the PPS control signal is then used to control the PPS 840 which supplies the braking signal to the brake 408. The LUT 830 is preferably adjusted according to the particular brake and strain gauge characteristics in order to achieve the appropriate force feedback and/or desired scaling thereof. The optional low pass filtering can be carried out using an RC low pass filter. The filter provides an optional electronic solution to mechanical vibrations at the end-effector 226.

Optionally, the feedback processing unit 800 displays the measured forces or a representative indications thereof on the monitor 152 so that the interventionalist may have a visual as well as tactile sense of the forces experiences by the needle 210. Additionally, if the force exceeds one or more determined thresholds, appropriate warning messages may be displayed on the monitor 152. For example, if the measured force is at or near a force that would indicate the needle 210 has contacted bone, a warning indicating the same may be displayed. Similarly, if the measured force is approaching a level large enough to puncture the myocardium wall of the heart, a warning to that effect may be displayed. Additionally, the LUT 830 may be so adjusted or tuned such that when one or more threshold forces are encountered, the brake 408 fully engages to substantially fix the shaft 402 against further rotation, thereby effectively halting further advancement of the needle 210 before the anatomy or tissue of concern is damaged or the patient 20 is otherwise harmed. Insomuch as the forces experiences on a biopsy needle as it encounters and/or pass through different tissue type may be known from experimental and/or historical data, by appropriately setting the mapping of force signals to PPS control signals, the LUT 830 may also optionally be tuned to enhance or exaggerate the tactile sensation when the tip of the needle 210 encounters a particular tissue type or pass from one tissue type to another.

Adjustment signals may also optionally be sent from the feedback processing unit 800 to the robot controller 700 and/or the virtual view processing unit 710. These signals allow the robot controller 700 and the virtual view processing unit 710 to adjust accordingly to forces and/or deflections experienced and measured by the strain gauge 230. For example, the adjustment signals from the feedback processing unit 800 are acted upon by the robot controller 700 to compensate for minor deflections experienced by the end-effector 226 which are measured by the strain gauge 230. The adjustment signals are also optionally used by the virtual view processing unit 710 to predict deviations of the needle from the planned trajectory 306 in the tissue due to forces on the needle and its orientation. In response thereto, suggested or recommended re-orientation of the needle's bevel or other corrective actions may be communicated to the interventionalist, e.g., with the extrapolated outcome thereof visualized in the virtual view shown on the monitor 152.

Further with respect to the feedback processing unit 800, preferably it is zeroed or a base line determined before each procedure. For example, the initial value output from the A/D converter 820 with the needle 210 at rest in air (i.e., having no external forces applied to it by operation of the procedure) is stored or saved. The stored value or base line is then subtracted from all subsequent output values from the A/D converter 820. In this manner, the digital signal output from the A/D converter 820 during the procedure is made relative to the initial needle conditions immediately preceding the procedure.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment(s), the invention is now claimed to be:

1. A system for conducting an image-guided medical procedure on a subject, the system comprising:
    a medical imaging apparatus which intermittently during the procedure obtains, upon demand, real-time medical images of the actual procedure;
    a robotic arm that holds a medical instrument used to perform the procedure, said robotic arm manipulating the medical instrument in response to a first signal;
    a detector which measures forces experienced by the medical instrument during the procedure and generates a second signal proportional thereto;
    a feedback circuit which receives the second signal and generates a third signal that has a non-linear relationship to the second signal;
    a haptic control, said haptic control generating the first signal in response to manipulations of an input device by an operator, said operator receiving tactile feedback from the haptic control in accordance with the third signal such that the tactile feedback has a non-linear relationship to the measured forces experienced by the medical instrument; and,
    a display which shows a virtual planning view of the procedure, said virtual planning view depicting a pre-procedure image of the subject with a virtual medical instrument corresponding to the medical instrument held by the robotic arm superimposed therein, said virtual medical instrument, in response to the first signal from the haptic control, having its position and orientation updated relative to the pre-procedure image.

2. The system according to claim 1, wherein the detector is a strain gauge, a load cell or a pressure sensor.

3. A system for conducting an image-guided medical procedure on a subject, the system comprising:
    a medical imaging apparatus which intermittently during the procedure obtains, upon demand, real-time medical images of the actual procedure;
    a robotic arm that holds a medical instrument used to perform the procedure, said robotic arm manipulating the medical instrument in response to a first signal;
    a gripper having an end-effector in which the medical instrument is held, said end-effector being mechanically joined to the gripper by at least one strain gauge and a plurality of resilient spring members, said resilient spring members and said strain gauge being arranged to protect against canting of the end-effector;
    a haptic control, said haptic control generating the first signal in response to manipulations of an input device by an operator, said operator receiving tactile feedback from the haptic control in accordance with forces measured by the strain gauge; and,
    a display which shows a virtual planning view of the procedure, said virtual planning view depicting a pre-procedure image of the subject with a depiction of the medical instrument held by the robotic arm superimposed therein.

4. The system according to claim 3, wherein the strain gauge and at least one of the resilient spring members are arranged juxtaposed to one another on opposite sides of the end-effector.

5. The system according to claim 3, wherein said detector generates a second signal responsive to the forces measured thereby, and further comprising:
    a feedback processing unit that in response to the second signal generates a third signal which is communicated to the haptic control, said haptic control producing the tactile feedback in response to the third signal.

6. A system for conducting an image-guided medical procedure on a subject, the system comprising:
    a medical imaging apparatus which intermittently during the procedure obtains, upon demand, real-time medical images of the actual procedure;
    a robotic arm that holds a medical instrument used to perform the procedure, said robotic arm manipulating the medical instrument in response to a first signal;
    a detector which measures forces experienced by the medical instrument during the procedure and generates a second signal indicative thereof;
    an amplifier which amplifies the second signal;
    an analog-to-digital converter which digitizes the amplified second signal;
    a look-up table which is accessed by the digitized second signal and maps the digitized second signal to a programmable power supply control signal;
    a programmable power supply which generates the third signal in response to the programmable power supply signal;
    a haptic control, said haptic control generating the first signal in response to manipulations of an input device by an operator, said operator receiving tactile feedback from the haptic control in accordance with the third signal; and,
    a display which shows images of the subject.

7. The system according to claim 6, wherein the look-up table is tuned such that the tactile feedback provided to the operator by the haptic control is essentially the same as would be experienced by the operator if the operator were to directly manipulate the medical instrument.

8. The system according to claim 6, wherein the look-up table is tuned to enhance the tactile feedback provided to the operator by the haptic control when the medical instrument transitions from one particular tissue type to another.

9. A system for conducting an image-guided medical procedure on a subject, the system comprising:
    a medical imaging apparatus which intermittently during the procedure obtains, upon demand, real-time medical images of the actual procedure;

a robotic arm that holds a medical instrument used to perform the procedure, said robotic arm manipulating the medical instrument in response to a first signal;

a detector which measures forces experienced by the medical instrument during the procedure;

a haptic control including:
  an input device which is manipulated by an operator;
  a shaft which rotates in response to the operator's manipulation of the input device;
  a brake which regulates how easy it is to rotate the shaft, said brake being responsive to the forces measured by the detector;
  an encoder which measures the rotation of the shaft and generates the first signal responsive thereto;

a display which shows a view of the procedure, said view depicting an image of the subject with an indication of the position and orientation of the medical instrument held by the robotic arm superimposed therein.

10. The system according to claim 9, wherein the input device is an auxiliary medical instrument coupled to the shaft, said auxiliary medical instrument substantially mimicking the medical instrument held by the robotic arm.

11. The system according to claim 9, wherein the haptic control further comprises:
  an adjustable mount for mounting the haptic control to a work surface, said adjustable mount including a joint that allows the operator to selectively orient the input device along a plurality of orientations regardless of the work surface's orientation.

12. The system according to claim 9, wherein when the measured force from the detector exceeds a determined threshold, the brake is fully engaged thereby substantially fixing the shaft against rotation.

13. A method of conducting a medical procedure on a subject, said method comprising:
  (a) planning the medical procedure, said planning including obtaining a pre-procedure image of the subject and superimposing therein a virtual medical instrument that corresponds to an actual medical instrument used to conduct the medical procedure;
  (b) remotely controlling a robotic arm holding the actual medical instrument to conduct the medical procedure;
  (c) measuring forces experienced by the actual needle as the medical procedure is being conducted;
  (d) providing tactile feedback to an operator conducting the procedure based on the measured forces, the tactile feedback varying in degree in different portions of the procedure;
  (e) updating a position and orientation of the virtual medical instrument in the pre-procedure image in accordance with the controlling of the robotic arm; and,
  (f) intermittently during the medical procedure, obtaining real-time images of the actual medical procedure.

14. The method according to claim 13, wherein step (b) comprises:
  manipulating an auxiliary medical instrument that substantially mimics the actual medical instrument such that the robotic arm manipulates the actual medical instrument in substantially the same manner.

15. A method of conducting a medical procedure on a subject, said method comprising:
  (a) planning the medical procedure, said planning including obtaining a pre-procedure image of the subject and superimposing therein a virtual medical instrument that corresponds to an actual medical instrument used to conduct the medical procedure and determining a threshold force which indicates an upper limit of the force which the actual medical instrument should be allowed to exert during the planned procedure;
  (b) remotely controlling a robotic arm holding the actual medical instrument to conduct the medical procedure by manipulating an auxiliary medical instrument that substantially mimics the actual medical instrument such that the robotic arm manipulates the actual medical instrument in substantially the same manner;
  (c) measuring forces experienced by the actual medical instrument as the medical procedure is being conducted;
  (d) providing tactile feedback to an operator conducting the procedure based on the measured forces;
  (e) substantially fixing the auxiliary medical instrument against manipulation when the measured forces exceed the determined threshold forces;
  (f) updating a position and orientation of the virtual medical instrument in the pre-procedure image in accordance with the controlling of the robotic arm; and,
  (g) intermittently during the medical procedure, obtaining real-time images of the actual medical instrument.

16. The method according to claim 13, further comprising:
  indicating to the operator when the measured forces exceed a determined threshold.

17. An apparatus for performing a medical procedure on a subject with a medical instrument, the apparatus comprising:
  imaging means for intermittently during the procedure obtaining, upon demand, real-time medical images of the actual procedure;
  robotic means for holding the medical instrument used to perform the procedure, said robotic means manipulating the medical instrument in response to a first signal;
  force detecting means for measuring forces experienced by the medical instrument during the procedure;
  control means for generating the first signal in response to manipulations of an input device by an operator and for providing said operator tactile feedback in accordance with the measured forces experienced by the medical instrument; and,
  display means for showing a virtual planning view of the procedure, said virtual planning view depicting a pre-procedure image of the subject with a virtual medical instrument corresponding to the medical instrument held by the robotic means superimposed therein, said virtual medical instrument, in response to the first signal from the control means, having its position and orientation updated relative to the pre-procedure image.

18. The apparatus according to claim 17, wherein the imaging means is a CT scanner, an MRI scanner, a fluoroscope, a SPECT scanner or a PET scanner.

19. The apparatus according to claim 17, wherein the force detecting means is a strain gauge, a load cell or a pressure sensor.

20. The apparatus according to claim 17, wherein the medical instrument is a biopsy needle.

* * * * *